United States Patent
Aristovich et al.

(10) Patent No.: US 6,576,798 B1
(45) Date of Patent: Jun. 10, 2003

(54) METHOD AND SYSTEM FOR PURIFYING CUMENE HYDROPEROXIDE CLEAVAGE PRODUCTS

(75) Inventors: Yuri Valerievich Aristovich, Lenigrad reg. (RU); Valeri Yurievich Aristovich, St. Petersburg (RU); John William Fulmer, Mt. Vernon, IN (US); Andrey Yurievich Sokolov, St. Petersburg (RU); Svetlana Ananyevna Ulyanova, St. Petersburg (RU); Sergey Nikolaevich Voyakin, St. Petersburg (RU)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/683,186

(22) Filed: Nov. 29, 2001

(51) Int. Cl.[7] .................. C07C 45/00; C07C 41/00; C07C 43/02; C07C 37/68; C07C 37/08
(52) U.S. Cl. ............ 568/383; 568/449; 568/741; 568/742; 568/754; 568/798
(58) Field of Search ................ 568/383, 741, 568/742, 754, 798, 449

(56) References Cited

U.S. PATENT DOCUMENTS

| 2,734,085 A | 2/1956 | Adams et al. |
|---|---|---|
| 2,744,143 A | 5/1956 | Filar |
| 2,992,169 A | 7/1961 | Gregory et al. |
| 3,335,070 A | 8/1967 | Adams |
| 3,437,699 A | 4/1969 | Flickinger |
| 3,454,653 A | 7/1969 | Larson |
| 3,692,845 A | 9/1972 | Cheema et al. |
| 3,862,244 A | 1/1975 | Genod et al. |
| 3,931,339 A | 1/1976 | Cooke |
| 3,965,187 A | 6/1976 | Little et al. |
| 4,092,360 A | 5/1978 | Van Peppen et al. |
| 4,298,765 A | 11/1981 | Cochran et al. |
| 4,334,107 A | 6/1982 | Van Peppen |
| 4,973,766 A | 11/1990 | Penzo et al. |
| 5,262,016 A | 11/1993 | Lorenzoni et al. |
| 5,264,636 A | 11/1993 | Shirahata et al. |
| 5,414,154 A | 5/1995 | Jenczewski et al. |
| 5,491,268 A | 2/1996 | Cipullo |
| 5,502,259 A | 3/1996 | Zakoshansky et al. |
| 5,510,543 A | 4/1996 | Fulmer et al. |
| 6,066,767 A | 5/2000 | Zakoshansky et al. |

Primary Examiner—Samuel Barts
Assistant Examiner—Sikarl A. Witherspoon

(57) ABSTRACT

A system for purifying a cumene hydroperoxide cleavage product mixture comprises a cumene hydroperoxide cleavage product mixture feed containing impurities in fluid communication with an aqueous alkaline solution feed; the cumene hydroperoxide cleavage product mixture and aqueous alkaline solution feeds in fluid communication with a neutralization drum having a aqueous salt phase outlet; a aqueous salt phase feed containing impurities in fluid communication with a decomposer reactor having an oxidized aqueous salt phase outlet; an oxidizing agent feed in fluid communication with the aqueous salt phase feed containing the impurities prior to the decomposer reactor; and an oxidized aqueous salt phase feed containing water-soluble oxidized derivatives of the impurities in fluid communication with the cumene hydroperoxide cleavage product mixture prior to the neutralization drum.

26 Claims, 1 Drawing Sheet

METHOD AND SYSTEM FOR PURIFYING CUMENE HYDROPEROXIDE CLEAVAGE PRODUCTS

BACKGROUND OF INVENTION

This disclosure relates to methods for phenol production and, more particularly, to methods and systems for purifying cumene hydroperoxide cleavage products.

Processes for preparing phenol from cumene are well known. The cumene method comprises two stages: the first one is cumene oxidation by air oxygen to cumene hydroperoxide (CHP), and the second one is CHP acidic catalytic cleavage (decomposition) to phenol and acetone. After producing and cleaving cumene hydroperoxide (CHP), the resultant cumene hydroperoxide cleavage product mixture contains phenol and acetone as the principal products together with varying amounts of impurities, e.g., alpha-methylstyrene, acetophenone, mesityl oxide, cumene, acetaldehyde, hydroxyacetone, and residual acid catalyst, e.g., sulfuric acid catalyst. Before the products can be recovered it is necessary to remove or neutralize the acid catalyst in the CHP cleavage product mixture since the presence of the acid catalyst in the subsequent distillations interferes with efficient recovery of the product and by-products of the reaction, in addition to causing corrosion of the distillation equipment.

Commercially, the residual sulfuric acid catalyst present in the cleavage product mixture is neutralized with an aqueous alkaline solution, e.g., aqueous sodium hydroxide. The resulting concentrated aqueous sodium sulfate salt solution formed from the sulfuric acid and the sodium hydroxide reaction is then separated from the main organic mixture using a series of liquid-liquid extraction operations. The resulting organic mixture, now free of sulfuric acid, is then subjected to a series of fractional distillations to recover the products and various components.

U.S. Pat. Nos. 2,734,085; 2,744,143; 3,931,339; and 5,510,543 variously teach conducting the cleavage acid extraction/neutralization step as a liquid-liquid extraction process in a reactor utilizing a circulating aqueous solution of concentrated sodium sulfate salt, i.e., the extractant, formed in situ by the reaction of sodium hydroxide and sulfuric acid. It is known that hydroxyacetone is typically present in an amount of 1,200–2,200 parts per million (ppm) concentration in the CHP cleavage product mixture prior to neutralization. During neutralization the hydroxyacetone equilibrates and partitions into two phases (organic and aqueous) within the neutralizer vessel in about equal concentrations. Hydroxyacetone is particularly troublesome to remove from phenol as it co-distills with phenol during the downstream rectification processes and contaminates the final phenol product. Although hydroxyacetone may be present in only minute quantities in the final phenol product, the hydroxyacetone impurity has color-forming tendencies and its presence renders the phenol product quality unacceptable for many end use applications, such as bisphenol A and polycarbonate.

To prevent this, U.S. Pat. Nos. 3,335,070; 3,454,653; 3,692,845; 5,502,259; and 6,066,767 variously teach removing hydroxyacetone from phenol via condensation reactions and conversion to higher boiling point materials, which create by-products that can be more easily separated from phenol in subsequent distillation steps. Both homogeneous and heterogeneous processes are described which use both basic and acidic treating agents on the organic streams to promote hydroxyacetone condensation reactions, such as sodium hydroxide, amines, ion exchange resins and zeolites. However, this treatment method is only partially effective because a new impurity 2-methybenzofuran (2MBF) forms, which is also very difficult to remove from phenol by distillation. This problem is particularly troublesome as its presence also renders the phenol product quality unacceptable for many end use applications.

In the conversion of hydroxyacetone to higher boiling point materials, U.S. Pat. No. 6,066,767 ('767 patent) describes a process for purifying phenol using sodium hydroxide and alkaline agents as treatment agents to promote deep condensation reactions of hydroxyacetone to high boiling point materials purportedly free of 2MBF. In this process the CHP cleavage product mixture is extracted with 10–20 weight percent (wt. %) sodium sulfate salt solution according to conventional methods, and the hydroxyacetone contained within the aqueous salt phase is treated with sodium hydroxide reagent to form deep condensation products which recycle into the process and mix with the phenol-acetone stream for later removal.

Several drawbacks are associated with the method of the '767 patent. First, there are high raw material costs associated with the neutralizing reagents. In the '767 method, to effectively neutralize the acidic 10–20 wt. % sodium sulfate aqueous stream large quantities of sodium hydroxide must be added to neutralize and maintain the excess alkalinity required to provide catalysis. In response to this quantity of sodium hydroxide additional sulfuric acid must be purchased and utilized to neutralize the sodium hydroxide so as to maintain the critical pH control range while neutralizing the CHP cleavage product mixture. Thus raw material costs are significant for the '767 process.

Secondly, alkaline phenol salts (e.g., sodium phenolate) form, which can cause pH fluctuations, incomplete phase separations during neutralization, and contribute to downstream fouling of equipment. If the alkaline phenol salts cause pH fluctuations, and the critical pH control range cannot be maintained, emulsions may form and render various equipment useless. Third, the '767 patent acknowledges that unidentified deep condensation products formed from hydroxyacetone re-enter the organic stream and recycle into the process. These unknown condensation products can potentially contaminate the final phenol product and risk causing other quality and equipment problems. Fourth, the process disclosed in the '767 patent employs multiple extraction stages to optimize the removal of hydroxyacetone. These multiple extraction stages require additional time, labor, materials and equipment to implement, thus increasing costs to remove hydroxyacetone to acceptable levels in the final phenol product.

Accordingly there remains a need in the art for a method and system for removing hydroxyacetone and other impurities from cumene hydroperoxide cleavage products to acceptable levels.

SUMMARY OF INVENTION

A method for removing impurities from a cumene hydroperoxide cleavage product mixture comprises reacting impurities in an aqueous salt phase with an oxidizing agent at a temperature and for a time in a non-alkaline environment sufficient to form water-soluble oxidized derivatives of the impurities; combining the aqueous salt phase containing the oxidizing agent and the water-soluble oxidized derivatives with a cumene hydroperoxide cleavage product mixture to further oxidize impurities in the combined product mixture; and separating the aqueous salt phase containing the water-soluble oxidized derivatives of the impurities from the combined product mixture.

In another embodiment, the method for removing impurities from a cumene hydroperoxide cleavage product mixture comprises reacting an aqueous salt phase containing impurities with an amount of oxidizing agent effective to maintain the pH of the reaction at about 3 to about 6 to form water-soluble oxidized derivatives of the impurities, wherein reacting comprises heating the aqueous salt phase containing the water-soluble oxidized derivatives and the oxidizing agent at a temperature of about 80 to about 140° Celsius for about 0.5 to about 1.5 hours under a pressure of about one atmosphere to about five atmospheres to the reaction mixture; combining the aqueous salt phase containing the oxidizing agent and the water-soluble oxidized derivatives with a cumene hydroperoxide cleavage product mixture to further oxidize impurities in the combined product mixture; and separating the aqueous salt phase containing the water-soluble oxidized derivatives of the impurities from the combined product mixture.

A system for purifying a cumene hydroperoxide cleavage product mixture comprises means for reacting an aqueous salt phase containing impurities with an oxidizing agent at a temperature and for a time sufficient to form water-soluble oxidized derivatives of the impurities; means for combining the aqueous salt phase containing the oxidizing agent and the water-soluble oxidized derivatives with a cumene hydroperoxide cleavage product mixture to further oxidize impurities in the combined product mixture; and means for separating the aqueous salt phase containing the water-soluble oxidized derivatives of the impurities from the combined product mixture.

In another embodiment, the system for purifying a cumene hydroperoxide cleavage product mixture comprises a cumene hydroperoxide cleavage product mixture feed containing impurities in fluid communication with an aqueous alkaline solution feed; the cumene hydroperoxide cleavage product mixture and aqueous alkaline solution feeds are in fluid communication with a neutralization drum having an aqueous salt phase outlet; an aqueous salt phase feed containing impurities in fluid communication with a decomposer reactor having an oxidized aqueous salt phase outlet; an oxidizing agent feed in fluid communication with the aqueous salt phase feed containing the impurities prior to the decomposer reactor; and an oxidized aqueous salt phase feed containing water-soluble oxidized derivatives of the impurities in fluid communication with the cumene hydroperoxide cleavage product mixture prior to the neutralization drum.

BRIEF DESCRIPTION OF DRAWINGS

Referring now to the FIGURE, which is merely illustrative, wherein the like elements are numbered alike, the FIGURE is a schematic flow diagram illustrating an exemplary embodiment of a system and method for removing impurities from cumene hydroperoxide cleavage products.

DETAILED DESCRIPTION

Figure 1:
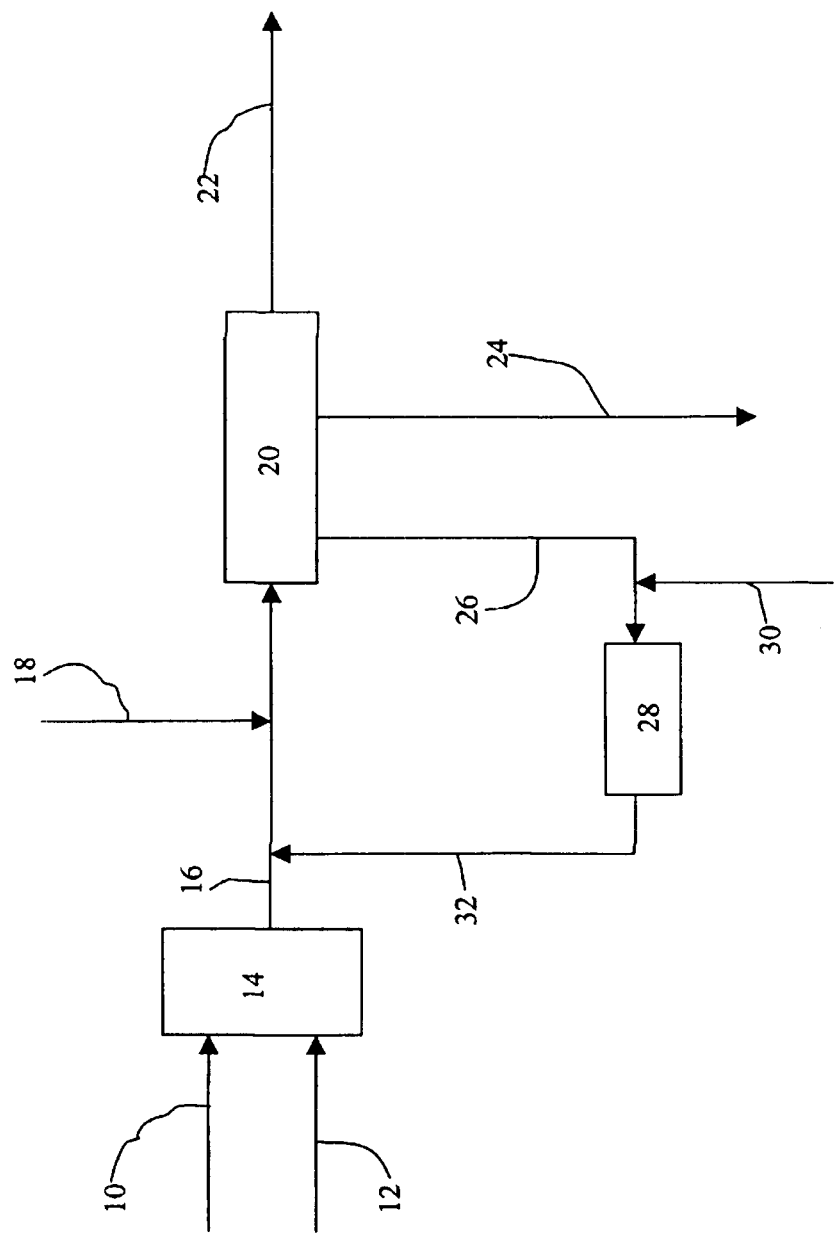

The inventors hereof have discovered that common impurities in phenol production can be oxidized to their water-soluble derivatives by the addition of oxidizing agents into the circulating neutralized aqueous phase stream. Quite unexpectedly, hydroxyacetone and aldehydes, e.g., acetaldehyde and propionaldehyde, present in this stream are effectively oxidized to water-soluble derivatives by the oxidation reaction. These oxidized derivatives are not heavy condensation products or high boiling point materials that can oxidize to form 2MBF. Instead, these water-soluble oxidized derivatives are extractable using existing equipment, and an additional reactor. This reactor eliminates the need for multiple extraction steps beyond existing equipment, and can be installed within existing phenol production schemes. Accordingly, the drawbacks of prior attempts employing condensation reactions and conversions to higher boiling point materials, and the like, are avoided or prevented by utilizing oxidizing agents.

An efficient method and system for commercial purification of CHP cleavage mixture products in phenol production comprises reacting impurities with an oxidizing agent in the presence of an aqueous salt phase at a temperature and for a time sufficient to form water-soluble oxidized derivatives of the impurities, and removing these oxidized impurities from the CHP cleavage product mixture. The method and system removes or eliminates impurities such as mesityl oxide, acetaldehyde, hydroxyacetone and various carbonyl-containing and aldehyde-containing impurities, and combinations comprising at least one of the foregoing impurities, in addition to some unreacted cumene and traces of other impurities, to acceptable levels in the final phenol product. For purposes of illustration, the process will be discussed in the context of removing hydroxyacetone from CHP cleavage product mixtures. However, other by-products and impurities, such as those mentioned above can also be removed effectively using the method and system disclosed herein.

The figure illustrates a flow chart showing in detail an embodiment of a system and method for removing hydroxyacetone from CHP cleavage product mixtures. A cumene hydroperoxide feed 10 ("CHP feed 10") and an acid catalyst feed 12, e.g., sulfuric acid, or other mineral acids, and the like, are fed into and mixed within a cumene hydroperoxide cleavage reactor 14 ("reactor 14") having a CHP cleavage product mixture outlet. A CHP cleavage product mixture feed 16 containing impurities exits reactor 14, and mixes with an aqueous alkaline solution such as aqueous hydroxide, and the like, (aqueous alkaline solution feed 18) downstream, prior to or when entering a neutralizer drum 20 ("drum 20") serially disposed after reactor 14, in an amount effective to neutralize any residual acid catalyst present and maintain the pH of the resulting neutralized cleavage product mixture within drum 20. The combined cleavage product mixture and aqueous alkaline solution feeds 16 and 18, respectively, comprise phenol, acetone, cumene, by-products and residual sulfuric acid, and an oxidized aqueous solution comprising about 10 to about 20 weight percent (wt. %) sodium sulfate solution containing water-soluble oxidized derivatives of impurities, which will be discussed below in further detail.

The amount of aqueous alkaline solution feed 18 may be controlled using a flow control device (not shown), e.g., a valve, that is actuated either manually or by an operator via an electronic interface (not shown), and may be optionally monitored using a sensor such as a pressure sensor, output sensor, flow rate sensor, mass flow sensor, and the like. Drum 20 contains an amount of aqueous alkaline solution effective to maintain the pH of the resulting neutralized cleavage product mixture at greater than or equal to about 1, preferably greater than or equal to about 3; and at a pH less than or equal to about 8, and preferably less than or equal to about 6.

The neutralized cleavage product mixture may be allowed to settle within drum 20, forming two distinct phases, a bottom aqueous phase and a top organic phase. The organic phase comprises phenol, acetone, cumene, mesityl oxide, alphamethylstyrene, acetophenone, dimethylbenzyl alcohol, cumylphenol, hydroxyacetone, various trace carbonyls and dissolved water, while the aqueous phase comprises about 10 to about 20 wt. % sodium sulfate solution (formed in situ within drum 20) containing impurities including but not limited to hydroxyacetone and acetaldehyde. The drum 20 includes an aqueous phase outlet, an aqueous phase purge outlet, and a neutralized cleavage product outlet, whereby the organic phase containing the neutralized cleavage product exits that outlet as neutralized cleavage product stream 22 for extraction using conventional techniques known to one skilled in the art. A portion of the aqueous phase containing undesired impurities is purged from drum 20 as aqueous phase purge 24, while the remaining aqueous phase proceeds downstream as aqueous phase stream 26 and flows downstream to a decomposer vessel 28 ("decomposer vessel 28"), having an oxidized aqueous phase stream outlet, and serially disposed after and in fluid communication with drum 20. Decomposer vessel 28 is preferably oriented within the system in fluid communication and in a continuous loop with drum 20, aqueous phase stream 26, oxidized aqueous phase stream 32 and CHP cleavage product mixture feed 16. The amount of impurities, e.g., hydroxyacetone, present in the aqueous phase stream 26 can be measured using quantitative analysis techniques, e.g., utilizing a Hewlett Packard gas chromatograph. Prior to, while entering, or within decomposer vessel 28, aqueous phase stream 26 combines and mixes with an oxidizing agent feed 30.

Oxidizing agent feed 30 is added to aqueous phase stream 26 in an amount effective to oxidize and decompose hydroxyacetone, and carbonyl-containing and aldehyde-containing impurities to water-soluble oxidized derivatives, which include acetic acid and pyruvic acid. These water-soluble oxidized derivatives are later removed in aqueous phase purge 24 as will be discussed below in further detail. Suitable oxidizing agents include but are not limited to oxygen (pure or atmospheric), hydrogen peroxide, sodium peroxide, potassium permanganate, sodium permanganate, and the like.

Decomposer vessel 28 can be maintained at a lower temperature of about 60 degrees Celsius (° C.), preferably about 70° C., most preferably about 80° C., to an upper temperature of about 160° C., preferably about 150° C., most preferably about 140° C., or a temperature range of about 80° C. to about 140° C., and at a lower pressure of about 0.25 atmosphere (atm), preferably about 0.50 atm, most preferably about 1 atm, to an upper pressure of about 8 atm, preferably about 7 atm, most preferably 6 atm, or a pressure range of the existing atmospheric pressure or about 1 atm to about 5 atm. The pH is monitored and controlled for decomposer vessel 28 by the amount of aqueous alkaline solution of feed 16 introduced into aqueous phase stream 26. Decomposer vessel 28 can be charged with an amount of aqueous alkaline solution effective to maintain a pH of the mixture of decomposition products and aqueous phase stream components at greater than about 3, preferably greater than about 4; and at a pH less than about 6, preferably less than about 5.

The rate of decomposition, or percent conversion, of hydroxyacetone to water-soluble oxidized derivatives can also be monitored, e.g., by quantitatively measuring the hydroxyacetone content of oxidized aqueous phase stream 32 using ion exclusion chromatography techniques, e.g., utilizing a DX100 Ion Chromatograph commercially available from the Dionex Corporation, Sunnyvale, Calif. The rate of decomposition, or likewise, oxidation, can be optimized by varying certain operating conditions such as the aqueous phase stream circulation rate, aqueous phase stream residence time within decomposer vessel 28, temperature, pressure, and the like. Likewise, removal of water-soluble oxidized derivatives can be optimized by varying the circulation rate of streams 16, 26, and 32. Thus, the amount of oxidizing agent added can also be changed based upon achieving the desired rate of percent conversion of the impurities to water-soluble oxidized derivatives.

The amount of hydroxyacetone present in oxidized aqueous phase stream 32 is compared with the amount of hydroxyacetone present in neutralized aqueous phase stream 26 to determine whether the desired percent conversion of hydroxyacetone to water-soluble oxidized hydroxyacetone derivatives is being achieved. The desired percent conversion of hydroxyacetone to oxidized hydroxyacetone derivatives is greater than about 40 percent, preferably greater than about 60 percent, most preferably greater than about 90 percent.

The resultant oxidized aqueous phase stream 32 exiting vessel 28 generally comprises an about 10 to about 20 wt. % sodium sulfate solution containing the water-soluble oxidized derivatives. To effectively maintain the pH within neutralizer drum 20 the oxidized aqueous phase stream 32 preferably combines with CHP cleavage product mixture feed 16 prior to entering drum 20. The resultant mixture is fed downstream, and combined and mixed with aqueous alkaline solution feed 18 to control the pH and reequilibrate the phase separation occurring within drum 20 as described earlier. The residual oxidizing agent present in the resultant mixture oxidizes impurities present within the aqueous salt phase. It is also believed that at least a portion of the impurities contained in the organic phase are also oxidized to form water-soluble derivatives, thus the cleaved cumene hydroperoxide product is further purified before undergoing distillation. As described earlier, a portion of the bottom aqueous phase is purged from drum 20 as aqueous phase purge 24, while the remaining aqueous phase exits drum 20 to decomposer vessel 28 as neutralized aqueous phase stream 26. The aqueous phase stream will continue recirculating from drum 20 to decomposer vessel 28 via neutralized aqueous phase feed 26, and back to drum 20 via oxidized aqueous phase feed 32 and cleavage product mixture feed 16. The circulation rate of these streams within the system is monitored to optimize the percent conversion of impurities to their water-soluble oxidized derivatives.

The method and system are further illustrated by the following non-limiting examples.

EXAMPLE 1

In a continuous process cumene was oxidized to form CHP, and the resultant CHP was subjected to acid cleavage using a sulfuric acid catalyst feed 12 in reactor 14 to form cleavage product mixture feed 16.

Table 1 illustrates the cleavage product mixture components in wt. % based on the total weight of the CHP cleavage product mixture feed 16 as measured by gas chromatography.

[t1]

| Component | Weight Percent (wt. %) |
|---|---|
| Phenol | 43.2% |
| Acetone | 39.0% |
| Cumene | 11.7% |
| Alphamethylstyrene | 3.1% |
| Water | 1.6% |
| Acetophenone | 0.7% |
| o,p-cumylphenol | 0.3% |
| Dimethylbenzyl alcohol | 0.1% |
| Hydroxyacetone | 0.16% |
| Acetaldehyde | 0.06% |
| Sulfuric acid | 0.03% |
| Mesityl oxide | 0.12% |

A 20 wt. % aqueous sodium hydroxide solution (stream 18) was added at a rate of 1,500 lbs/hr to the cleavage product mixture feed 16, having a feed rate of 200,000 lbs/hr, in an amount effective to neutralize the residual sulfuric acid present and provide a pH of 4.5 in neutralization drum 20. The resulting organic phase contained a hydroxyacetone concentration of 1550 parts per million (ppm), while the aqueous phase contained an 18 wt. % sodium sulfate solution having a hydroxyacetone concentration of 1480 ppm and an acetaldehyde concentration of 300 ppm as measured using an HP5890 gas chromatography and a Dionex DX100 ion-chromatograph.

The aqueous phase was withdrawn from the bottom of the neutralizer drum 20, as neutralized aqueous phase stream 26, and pumped into decomposer vessel 28 at a rate of 500,000 lbs/hr. The decomposer vessel 28 was maintained at a temperature of 90° C. and one atm pressure for one hour without utilizing treating agents. The hydroxyacetone concentration in the resulting heat-treated stream fed forward from the decomposer vessel 28 was measured at 1210 ppm. This represents a hydroxyacetone conversion of 18.2% using heat treatment alone. The neutralized aqueous phase stream 26 and heat-treated aqueous phase streams were analyzed using a Dionex DX100 ion exclusion chromatographs and determined to contain 80 ppm of pyruvic acid.

Following recirculation at a rate of 500,000 lbs/hr of the heat-treated stream and subsequent mixing and reequilibration with cleavage product mixture stream 16 in neutralizer drum 20, the hydroxyacetone concentration of neutralized cleavage product mixture stream 22 was measured at 1320 ppm using gas chromatography analysis.

EXAMPLE 2

A second trial was conducted utilizing the same raw materials and conditions used in Example 1, except that the decomposer vessel 28 was operated at the following parameters: 135° C., 6 atm pressure, and 1 hour residence time. Again, as in Example 1, an oxidizing agent was not utilized. The hydroxyacetone content in the resultant heat and pressure treated, non-oxidized aqueous phase stream was measured at 870 ppm. This concentration represents a 44.6% hydroxyacetone conversion when employing elevated heat treatment and super atmospheric pressure conditions. Following recirculation of the heat and pressure treated, non-oxidized aqueous phase stream, and re-equilibration within neutralizer reactor 20, the hydroxyacetone concentration of neutralized cleavage product stream 22 was measured at 1090 ppm.

EXAMPLE 3

A third trial was conducted utilizing the same raw materials and conditions used in Example 1, except that a hydrogen peroxide oxidizing agent was utilized. The hydrogen peroxide oxidizing agent was added to decomposer vessel 28 as a 30 wt. % aqueous solution in an amount effective to establish a 0.5 wt. % hydrogen peroxide concentration. The hydroxyacetone concentration of the resultant oxidized aqueous phase stream 32 was measured at 210 ppm. This concentration represents an 85.8% hydroxyacetone conversion to water-soluble oxidized derivatives. Following recirculation of oxidized aqueous phase stream 32 and reequilibration within neutralizer drum 20, the hydroxyacetone concentration of the neutralized cleavage product stream 22 was measured at 690 ppm. The acetaldehyde concentration of the oxidized aqueous phase stream 32 was measured at 120 ppm, representing a 60% acetaldehyde conversion. A qualitative analysis of oxidized aqueous phase stream 32 and aqueous phase purge 24 using a DX100 ion chromatograph indicated 750 ppm of pyruvic acid and 1320 ppm of acetic acid in both streams.

EXAMPLE 4

A second trial based upon Example 3 was conducted utilizing the same raw materials and conditions of Example 3, except that decomposer vessel 28 was charged with a 0.06 wt. % sodium hydroxide aqueous solution in addition to the 0.5 wt. % hydrogen peroxide oxidizing agent. A qualitative analysis measured a hydroxyacetone concentration of 108 ppm in oxidized aqueous phase stream 32. This concentration represents a 92.7% hydroxyacetone conversion to water-soluble oxidized derivatives. Following recirculation of oxidized aqueous phase stream 32 and re-equilibration within neutralizer drum 20, a qualitative analysis of neutralized cleavage product mixture 22 indicated a hydroxyacetone concentration of 590 ppm and an acetaldehyde concentration of 110 ppm. A qualitative analysis of aqueous phase purge 24 indicated a pyruvic acid sodium salt concentration of 812 ppm, and a sodium acetate concentration of 1250 ppm.

EXAMPLE 5

A third trial based on Example 3 was conducted utilizing the same raw materials and conditions of Example 3, except that decomposer vessel 28 was charged with a 0.5 wt. % concentration of potassium permanganate as the oxidizing agent rather than a 0.5 wt. % hydrogen peroxide oxidizing agent. The pH within decomposer vessel 28 was maintained between 4 to 5. A qualitative analysis of oxidized aqueous phase stream 32 measured a hydroxyacetone concentration of 305 ppm and an concentration of 35 ppm, and an identical analysis of aqueous phase purge 24 indicated a pyruvic acid concentration of 610 ppm. Following recirculation and after re-equilibration, a qualitative analysis of neutralized cleavage product mixture stream 22 measured a hydroxyacetone concentration of 790 ppm.

[t2]

Hydroxyacetone Concentration of Streams (parts per million)

| Example No. | Stream 16 | Stream 26 | Stream 32 | Stream 22 |
|---|---|---|---|---|
| 1 | 1550 | 1480 | 1210 | 1320 |
| 2 | 1550 | 1480 | 870 | 1090 |
| 3 | 1550 | 1480 | 210 | 690 |

-continued

[t2]

Hydroxyacetone Concentration of Streams
(parts per million)

| Example No. | Stream 16 | Stream 26 | Stream 32 | Stream 22 |
|---|---|---|---|---|
| 4 | 1550 | 1480 | 108 | 590 |
| 5 | 1550 | 1480 | 305 | 820 |

The method and system for removing hydroxyacetone from a phenol-acetone mixture possesses several advantages such as reduced time, labor, equipment and costs associated with conventional purification methods, while also improving the quality of the final phenol product.

In particular, the inventive method and system employs oxidizing agents rather than troublesome additional alkaline agents or condensation and conversion reactions. There are accordingly none of the higher boiling point materials or 2-methybenzofuran as products, fouling of equipment due to overly acidic or alkaline process conditions, or fluctuations in pH, each of which may require complex systems to overcome. The inventive method and system thus alleviates the need for complex systems and expensive equipment, and requires a lower initial plant investment, as there is, except for an additional vessel, no requirement for special or additional equipment for multiple extraction and/or distillation steps.

The inventive method and system also eliminates or prevents the formation of heavy condensation products or high boiling point materials that foul downstream equipment and affect the quality of the final phenol products. Water-soluble oxidized derivatives of impurities such as hydroxyacetone and acetaldehyde are formed, separated in existing equilibration steps, and purged without employing additional distillation/extraction steps or equipment. As a result, existing facilities can quickly implement this inventive method and system, and recognize immediate benefits.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A method for removing impurities from a cumene hydroperoxide cleavage product mixture, comprising:

extracting impurities from a first cumene hydroperoxide cleavage product mixture with an aqueous phase having a basis pH;

neutralizing the aqueous phase to form an aqueous salt phase;

oxidizing the impurities in the aqueous salt phase with an oxidizing agent to form water-soluble oxidized derivatives of the impurities;

extracting impurities in a second cumene hydroperoxide cleavage product mixture with the aqueous salt phase containing the oxidizing agent and the water-soluble oxidized derivatives; and separating, from the extracted second cumene hydroperoxide cleavage product mixture, the aqueous salt phase containing the water-soluble oxidized derivatives from the first product mixture and the extracted impurities from the second product mixture.

2. The method of claim 1, wherein extraction of the second product mixture is in the presence of at least a portion of the first product mixture.

3. The method of claim 1, wherein greater than about 40 percent of the impurities are converted to the water-soluble oxidized derivatives.

4. The method of claim 1, wherein greater than about 60 percent of the impurities ate converted to the water-soluble oxidized derivatives.

5. The method of claim 1, wherein greater than about 90 percent of the impurities are converted to the water-soluble oxidized derivatives.

6. The method of claim 1, wherein the impurities are mesityl oxide, acetaldehyde, hydroxyacetone, carbonyl-containing impurities, aldehyde-containing impurities, or a combination comprising at least one of the foregoing impurities.

7. The method of claim 1, wherein the oxidizing agent oxidizes impurities extracted from the second product mixture.

8. The method of claim 1, wherein the oxidizing agent is present in an amount effective to maintain a pH of about 3 to about 6 during oxidizing.

9. The method of claim 1, wherein the oxidizing agent is present in an amount effective to maintain a pH of about 4 to about 5 during oxidizing.

10. The method of claim 1, wherein the aqueous salt phase further comprises about 10 to about 20 weight percent sodium sulfate solution.

11. The method of claim 1, wherein the oxidizing agent is oxygen, hydrogen peroxide, sodium peroxide, potassium permanganate, sodium permanganate, or a combination comprising at least one of the foregoing oxidizing agents.

12. The method of claim 1, wherein the temperature is about 80 to about 140° Celsius.

13. The method of claim 1, wherein reacting further comprises applying a pressure of about 0.5 to about 5 atmospheres.

14. The method of claim 1, wherein the time is about 0.5 to about 1.5 hours.

15. A method for removing impurities from a cumene hydroperoxide cleavage product mixture, comprising:

extracting impurities from a first cumene hydroperoxide cleavage product mixture with an aqueous phase;

neutralizing the aqueous phase to form an aqueous salt phase;

reacting the aqueous salt phase containing impurities with an amount of oxidizing agent effective to maintain the pH of the reaction at about 3 to about 6, at a temperature of about 80 to about 140° Celsius, for about 0.5 to about 1.5 hours under a pressure of about one atmosphere to about five atmospheres, to oxidize the impurities to water-soluble oxidized derivatives;

extracting the impurities in a second cumene hydroperoxide cleavage product mixture with the aqueous salt phase containing the oxidizing agent and the water-soluble oxidized derivatives; and separating, from the extracted second cumene hydroperoxide cleavage product mixture, the aqueous salt phase containing the water-soluble oxidized derivatives of the impurities from the first product mixture and the impurities from the second product mixture.

16. The method of claim 15, wherein the oxidizing agent is oxygen, hydrogen peroxide, sodium peroxide, potassium permanganate, sodium permanganate, or a combination comprising at least one of the foregoing oxidizing agents.

17. The method of claim 15, wherein the oxidizing agent is present in an amount effective to maintain the pH at about 4 to about 5 during oxidizing.

18. The method of claim 15, wherein the impurities are mesityl oxide, acetaldehyde, hydroxyacetone, carbonyl-containing impurities, aldehyde containing impurities, or combinations comprising at least one of the foregoing impurities.

19. A system for purifying a cumene hydroperoxide cleavage product mixture, comprising:
   means for extracting impurities from a first cumene hydroperoxide cleavage product mixture with an aqueous phase;
   means for neutralizing the aqueous phase to form an aqueous salt phase;
   means for reacting the aqueous salt phase containing the impurities with an oxidizing agent to form water-soluble oxidized derivatives of the impurities;
   means for extracting a second cumene hydroperoxide cleavage product mixture with the aqueous salt phase containing the oxidizing agent and the water-soluble oxidized derivatives, wherein the means for extracting the first and second cumene hydroperoxide cleavage product mixtures may be the same or different; and
   means for separating, from the extracted second cumene hydroperoxide cleavage product mixture, the aqueous salt phase containing the water-soluble oxidized derivatives from the first product mixture and the extracted impurities from the second product mixture.

20. The system of claim 19, further comprising means for combining the aqueous salt phase containing the water-soluble oxidized derivatives with a cumene hydroperoxide cleavage product mixture.

21. The system of claim 19, further comprising means for removing the oxidized derivatives from the combined aqueous salt phase/cumene hydroperoxide cleavage product mixture.

22. A system for purifying a cumene hydroperoxide cleavage product mixture, comprising:
   a cumene hydroperoxide cleavage product mixture containing impurities feed and aqueous alkaline solution feeds in fluid communication with a neutralization drum having an aqueous salt phase outlet, wherein the aqueous salt phase outlet is in fluid communication with a decomposer reactor having an oxidizing agent feed and an oxidized aqueous salt phase outlet, wherein the oxidized aqueous salt phase outlet is in fluid communication with the cumene hydroperoxide cleavage product mixture containing impurities feed prior to the neutralization drum.

23. The system of claim 22, wherein the neutralization drum is in fluid communication with and serially disposed prior to the decomposer reactor.

24. The system of claim 22, wherein the neutralization drum has an aqueous salt phase purge outlet and a neutralized cumene hydroperoxide cleavage product mixture outlet.

25. The system of claim 22, wherein the oxidizing agent feed is oxygen, hydrogen peroxide, sodium peroxide, potassium permanganate, sodium permanganate, or a combination comprising AL least one of the foregoing oxidizing agents.

26. The system of claim 22, wherein the impurities are alpha-methylstyrene, acetophenone, dimethylbenzyl alcohol, cumylphenol, mesityl oxide, acetaldehyde, hydroxyacetone, carbonyl-containing impurities, aldehyde-containing impurities, or a combination comprising at least one of the foregoing impurities.

* * * * *